United States Patent [19]

Takayanagi et al.

[11] Patent Number: 5,220,065

[45] Date of Patent: Jun. 15, 1993

[54] METHOD FOR PRODUCING N-METHYLOLACRYLAMIDE

[75] Inventors: Yasuyuki Takayanagi; Kiyobmi Takahashi; Tomio Nakamura, all of Yokohama, Japan

[73] Assignee: Nitto Chemical Industry Co., Ltd., Tokyo, Japan

[21] Appl. No.: 865,270

[22] Filed: Apr. 8, 1992

[30] Foreign Application Priority Data

| Apr. 12, 1991 | [JP] | Japan | 3-106385 |
| Apr. 22, 1991 | [JP] | Japan | 3-116666 |
| Aug. 2, 1991 | [JP] | Japan | 3-216526 |

[51] Int. Cl.$^5$ .......................... C07C 233/17
[52] U.S. Cl. ...................... 564/208; 564/192; 564/204
[58] Field of Search ......................... 564/208

[56] References Cited

U.S. PATENT DOCUMENTS

| 2,760,977 | 8/1956 | Feuer et al. | 564/208 |
| 2,864,861 | 12/1958 | Wohnsiedler et al. | 564/208 |
| 3,064,050 | 11/1962 | Saunder et al. | 564/208 |
| 3,087,965 | 4/1963 | Dowbenko et al. | 564/208 |
| 3,280,189 | 10/1966 | Cline | 564/208 |
| 3,712,926 | 1/1973 | Petersen | 564/208 |
| 3,887,618 | 6/1975 | Hein | 564/208 |

FOREIGN PATENT DOCUMENTS

| 49-14418 | 2/1974 | Japan . |
| 49-36615 | 4/1974 | Japan . |
| 49-127912 | 12/1974 | Japan . |
| 142146 | 6/1987 | Japan | 564/208 |

Primary Examiner—Richard L. Raymond
Assistant Examiner—Shailendra Kumar
Attorney, Agent, or Firm—Cushman, Darby & Cushman

[57] ABSTRACT

A method for producing N-methylolacrylamide which comprises reacting acrylamide with formaldehyde or paraformaldehyde in an aqueous solvent in the presence of (A) a basic compound and at least one member selected from the group consisting of a salt of Mo-containing acid and a salt of W-containing acid, or (B) a quaternary ammonium hydroxide compound, is provided by the present invention. According to the method of the present invention, N-methylolacrylamide having few by-products is obtained in high yields.

9 Claims, No Drawings

METHOD FOR PRODUCING N-METHYLOLACRYLAMIDE

BACKGROUND OF THE INVENTION

1. Field of the Invention

The present invention relates to a method for producing N-methylolacrylamide by reacting acrylamide with formaldehyde or paraformaldehyde.

N-methylolacrylamide is a crosslinkable monomer widely used in fiber treatments, photosensitive resins, adhesives, paints and the like.

2. Description of the Related Art

Various methods for producing N-methylolacrylamide by hydroxymethylation of acrylamide with formaldehyde are so far known. For example, there are proposed a method of reacting a 60 to 97% aqueous acrylamide solution with formaldehyde in an aqueous solvent using an alkali catalyst (U.S. Pat. No. 3,064,050), a method of reacting acrylamide with formaldehyde without a solvent using a tertiary amine (e.g. triethylamine, triethanolamine) as catalyst (U.S. Pat. No. 2,864,861), a method of reacting acrylamide with formaldehyde in water or an organic solvent or without a solvent using a basic anion exchange resin as catalyst (Japanese Patent Application Kokai No. 49-14418, No. 49-36615 and No. 49-127912), etc.

However, these conventional N-methylolacrylamide-manufacturing methods have many problems to be improved to use them in industry. That is, side reactions cannot sufficiently be inhibited, so that by-products are accumulated in the reaction solution to lower the yield of N-methylolacrylamide; troublesome purification processes are required to obtain high-purity N-methylolacrylamide from the reaction solution; the amount of the catalyst used is large; and the catalyst is relatively expensive.

SUMMARY OF THE INVENTION

The present invention was made to solve the problems of the conventional methods. Its object is to provide a method for producing N-methylolacrylamide which can be advantageously applied in industry, and more specifically a method for producing high-purity N-methylolacrylamide in high yields by improving reaction selectivity to inhibit side reactions.

The present inventors have made an extensive study to attain the above objects, and as a result have found that when N-methylolacrylamide is produced by hydroxymethylation of acrylamide with formaldehyde or paraformaldehyde, side reactions are inhibited and the desired product is obtained in high selectivity by using as a catalyst a basic compound and at least one member selected from the group consisting of a salt of molybdenum (Mo)-containing acid and a salt of tungsten (W)-containing acid, or a quaternary ammonium hydroxide compound. The present inventors thus attained to the present invention.

DESCRIPTION OF THE PREFERRED EMBODIMENTS

The present invention relates to a method for producing N-methylolacrylamide characterized by reacting acrylamide with formaldehyde or paraformaldehyde in an aqueous solvent in the presence of (A) a basic compound and a salt of Mo-containing acid and/or a salt of W-containing acid, or (B) a quaternary ammonium hydroxide compound.

The embodiment of the present invention will be illustrated below.

The reaction of acrylamide with formaldehyde or paraformaldehyde in the present invention is carried out using a particular compound as catalyst in a reaction medium so that the reaction system forms a uniform solution.

Acrylamide, a starting material, used in the present invention may be of any form of aqueous solution and crystal. Formaldehyde is preferably used in the form of aqueous solution, and a commercially available 37% formalin may be used. As to paraformaldehyde, commercially available products of 70 to 95% in purit may likewise be used.

The ratio of acrylamide and formaldehyde or paraformaldehyde used in the reaction is 0.5 to 2 moles, preferably 0.8 to 1.5 moles of formaldehyde based on 1 mole of acrylamide, provided that the amount of paraformaldehyde is converted to that of formaldehyde.

The aqueous solvent used as reaction medium is a solvent for acrylamide, formaldehyde and paraformaldehyde, it including water and a mixed solvent of water and an organic solvent soluble in water. The organic solvent includes methanol, ethanol, acetone and the like. When the mixed solvent is used, the proportion of water is preferably 50 wt. % or more. The amount of the aqueous solvent used is preferably such a one as giving about 30 to about 90 wt. % acrylamide solution.

The basic compound used as catalyst in the present invention includes hydroxides of alkali metals or alkaline earth metals such as lithium hydroxide, sodium hydroxide, potassium hydroxide, rubidium hydroxide, calcium hydroxide, barium hydroxide, etc.; salts of alkali metals or alkaline earth metals such as sodium carbonate, potassium carbonate, sodium phosphate, disodium hydrogenphosphate, sodium pyrophosphate, potassium phosphate, dipotassium hydrogenphosphate, sodium borate, sodium aluminate, sodium silicate, etc.; tertiary amines such as trimethyalmine, triethylamine, triethanolamine, N-ethylmorpholine, N,N-diethylhydroxylamine, etc.; metal alkoxides such as sodium methoxide, potassium ethoxide, etc.; and basic anion exchange resins such as Amberlite® IRA400, Amberlyst® A26, etc. Among these, preferred basic compounds are alkali metal hydroxides such as sodium hydroxide, potassium hydroxide, etc., alkali metal salts such as sodium carbonate, potassium carbonate, sodium phosphate, disodium hydrogenphosphate, potassium phosphate, dipotassium hydrogenphosphate, sodium silicate, etc., and tertiary amines such as trimethylamine, triethylamine, triethanolamine, etc.

The amount of the basic compound used is selected from the range of 0.001 to 10 mole %, preferably 0.01 to 5 mole % based on 1 mole of acrylamide.

The salt of Mo-containing acid includes molybdates and salts of Mo-containing heteropolyacids, and specifically includes alkali metal molybdates such as lithium molybdate, sodium molybdate, potassium molybdate, etc., alkali metal phosphomolybdates such as lithium phosphomolybdate, sodium phosphomolybdate, etc. and alkali metal silicomolybdates such a lithium silicomolybdate, sodium silicomolybdate, etc.

The salt of W-containing acid includes tungstates and salts of W-containing heteropolyacids, and specifically includes alkali metal tungstates such as lithium tungstate, sodium tungstate, potassium tungstate, etc., alkali metal phosphotungstates such as lithium phosphotungstate, sodium phosphotungstate, etc., and alkali metal silicotungstates such as lithium silicotungstate, sodium silicotungstate, etc. These molybdates and tungstates can be used in mixture of two or more of them.

The amounts of these salts of Mo-containing and/or W-containing acid are selected from the range of 0.1 to 20 moles, preferably 0.5 to 12 moles based on 1 mole of the coexisting basic compound.

The quaternary ammonium hydroxide compound includes tetramethylammonium hydroxide, tetraethylammonium hydroxide, tetrapropylammonium hydroxide, tetrabutylammonium hydroxide, trimethylbenzylammonium hydroxide, cetylethyldimethylammonium hydroxide, cetyldimethylbenzylammonium hydroxide, hexadecyltrimethylammonium hydroxide, trioctylmethylammonium hydroxide, cetylpyridinium hydroxide and the like. The above quaternary ammonium hydroxide compounds may be used in combination with sodium hydroxide, sodium phosphate, trimethylamine or triethylamine.

The amount of the quaternary ammonium hydroxide compound is selected from the range of 0.001 to 10 mole %, preferably 0.01 to 5 mole % based on 1 mole of acrylamide.

From the overall standpoints of reaction rate, yield, inhibition of side reactions and the like, it is preferred to carry out the reaction of the present invention at a reaction temperature ranging from 20° to 80° C., preferably 30° to 60° C. while maintaining the pH of the reaction solution at 7 or more, preferably 8 to 12. After completion of the reaction, the pH of the reaction solution is adjusted with a mineral acid (e.g. sulfuric acid, hydrochloric acid) so as to be in a range of 6 to 8. When the pH is less than 6, bis-form products such as methylenebisacrylamide, diacrylamide dimethyl ether and the like are produced as by-products to remarkably lower the purity to the desired product. An increased amount of the bis-form products makes it difficult to use the desired product as a polymerized product because the solubility of the polymerized product remarkably lowers. Further, when the pH is more than 8, decomposition and polymerization of the desired product occur at the same time to remarkably lower the purity of the desired product.

According to the method of the present invention, aqueous N-methylolacrylamide solutions containing few by-products are obtained. When this aqueous solution is a high-concentration one obtained with an aqueous acrylamide solution having a concentration of about 60 wt. % or more, high-purity N-methylolacrylamide can easily be obtained as crystal by cooling and crystallization. When this aqueous solution is a low-concentration one obtained with an aqueous acrylamide solution having a concentration ranging from about 30 to about 60 wt. %, the same high-purity N-methylolacrylamide can easily be obtained as crystal by concentration of the reaction solution, crystallization and separation.

Concentration of the reaction solution is preferably carried out under the conditions wherein the degree of reduced pressure is in a range of 10 to 300 mmHg, preferably 20 to 150 mmHg, the concentration temperature is in a range of 30° to 80° C., preferably 40° to 70° C. and the pH of the concentrated solution is in a range of 6 to 8. When the concentration temperature is more than 80° C., polymerization occurs suddenly to solidify the entire concentrated solution. When it is less than 30° C., the concentration requires a long period of time. When the pH of the concentrated solution is less than 6, bis-form products such as methylenebisacrylamide, diacrylamide dimethyl ether and the like are produced as by products. When it is more than 8, hydrolysis and base-catalyzed polymerization of the reaction product occur. The concentration is carried out until the concentration of N-methylolacrylamide is about 60 to about 90 wt. %. When the reaction solution is concentrated to more than 90 wt. %, it becomes very easy to polymerize to cause sudden polymerization and solidification of the entire concentrated solution. During the concentration, concurrence of the polymerization can be inhibited by introducing oxygen or air into the reaction solution and if necessary adding a polymerization inhibitor. The polymerization inhibitor which can be used includes hydroquinone, p-methoxyphenol, 2,6-di-tert-butylcatechol, phenothiazine, cupferron, hydroxylamine sulfate, sodium nitrite, copper chloride, copper nitrate, oxalic acid and the like.

Crystallization of N-methylolacrylamide is carried out by cooling the reaction solution or concentrated solution to a range of 0° to 50° C. and separating precipitated crystals.

The mother liquor after separation of crystal is used to further precipitate N-methylolacrylamide crystals by concentrating and cooling it again, or recycled to the next reaction.

The method of the present invention is practiced further advantageously industrially by modifying it to a continuous process.

According to the method of the present invention, N-methylolacrylamide having few by-products is obtained in the form of aqueous solution. Further, high-purity, crystalline N-methylolacrylamide having a uniform and large particle size of crystal can be obtained in high yields from this reaction solution.

N-methylolacrylamide has a good solubility, so that the mother liquor after separation of N-methylolacrylamide from the reaction solution still contains the desired product, N-methylolacrylamide, in large amounts together with the unreacted materials. The method of the present invention products very few by-products, so that it is easy to use this mother liquor after separation for recycling unlike the conventional methods.

Further, the N-methylolacrylamide-containing solution obtained by the method of the present invention may be used as it is without isolating it, for example, to synthesize N-methylolacrylamide derivatives such as N-butoxymethylacrylamide, N-dimethylaminomethylacrylamide and the like.

It is known here that the aqueous N-methylolacrylamide solution produces impurities, particularly N,N'-methylenebisacrylamide, a crosslinkable substance, with the lapse of time, in other words, it is an unstable substance (Japanese Patent Application Kokai No. 62-175449). In the method of the present invention, however, it is beyond expectation that the reaction solution containing N-methylolacrylamide, even if concentrated, causes no side reactions such as condensation, polymerization and the like, thereby giving high-purity crystalline N-methylolacrylamide.

The present invention will be illustrated more specifically with reference to the following examples, which are not however to be interpreted as limiting the invention thereto.

EXAMPLE 1

To a 200 ml reactor equipped with a stirrer, thermometer and pH meter were added 60 g of crystalline acrylamide and 14 g of water, and the acrylamide was dissolved in water at an inner temperature of 50° C. Thereafter, a mixed aqueous solution of sodium hydroxide and sodium molybdate (sodium hydroxide concentration, 1.0%; and molar ratio of sodium molybdate to sodium hydroxide, 2:1) was added thereto as catalyst to adjust the pH of the solution to 10. Thereafter, 27.2 g of 95% paraformaldehyde was added, and reaction was carried out while maintaining the pH of the reaction solution at 10 with the above catalyst solution. The amount of the catalyst solution [sodium hydroxide content, 0.008 g (0.0002 mole); and sodium molybdate content, 0.082 g (0.0004 mole)] required for reaction was 0.8 g. The reaction solution was analyzed by high-performance liquid chromatography to find that at a point when 1 hour passed after beginning of reaction, the yield (%), where the yield (%) is calculated by dividing the moles of N-methylolacrylamide present in reaction solution by the moles of acrylamide fed into the reaction solution and multiplying by 100, of N-methylolacrylamide in the reaction solution was 93.0%, and the yield (%), where the yield (%) is calculated by dividing the moles of by-products present in reaction solution by the moles of acrylamide fed into the reaction solution and multiplying by 100, of by-products in the solution was 0.2%.

EXAMPLES 2 TO 14

Using the catalysts and reaction conditions shown in Table 1, reaction of acrylamide with formaldehyde or paraformaldehyde was carried out in the same manner as in Example 1.

EXAMPLE 15

To a 200 ml reactor equipped with a stirrer, thermometer and pH meter was added 120 g of a 50% aqueous acrylamide solution, and the inner temperature was raised to 50° C. Thereafter, a mixed aqueous solution of sodium hydroxide and sodium molybdate (sodium hydroxide concentration, 1.0%; and molar ratio of sodium molybdate to sodium hydroxide, 2:1) was added thereto as catalyst to adjust the pH of the solution to 10. Thereafter, 27.2 g of 95% paraformaldehyde was added, and reaction was carried out while maintaining the pH of the reaction solution a 10 with the above catalyst solution. The amount of the catalyst solution sodium hydroxide content, 0.008 g (0.0002 mole); and sodium molybdate content, 0.082 g (0.0004 mole)] required for reaction was 0.8 g. At a point when 1 hour passed after beginning of reaction, the reaction solution was analyzed by high-performance liquid chromatography to find that the yield (%) of N-methylolacrylamide in the reaction solution was 93.0%, and the content of by-products in the solution was 0.2%. After this reaction solution was neutralized to a pH of 7 with an 1 N aqueous sulfuric acid solution, it was concentrated at 50° C. under a reduced pressure of 100 to 150 mmHg until the N-methylolacrylamide concentration was 75% while introducing a small quantity of air through a capillary into the reaction solution. The concentrated solution thus obtained was slowly cooled to 2° C. and filtered to obtain 43.5 g of crystalline N-methylolacrylamide. Analysis by high-performance liquid chromatography showed that the purity of N-methylolacrylamide was 99.0%.

EXAMPLES 16 TO 22

Using the acrylamide concentrations, catalysts, reaction conditions and crystallization conditions shown in Table 1, reaction of acrylamide with formaldehyde or paraformaldehyde was carried out in the same manner as in Example 1. After completion of the reaction, the reaction solution was concentrated under reduced pressure to crystallize and separate N-methylolacrylamide.

EXAMPLE 23

After reaction was carried out in the same manner as in Example 1, the reaction solution was cooled to 5° C. and filtered to obtain 42.3 g of crystalline N-methylolacrylamide. Analysis by high-performance liquid chromatography showed that the purity of N-methylolacrylamide was 99.0%.

COMPARATIVE EXAMPLE 1

Reaction was carried out in the same manner as in Example 1 except that sodium hydroxide alone was used as catalyst.

COMPARATIVE EXAMPLE 2

Reaction was carried out in the same manner as in Example 15 except that sodium hydroxide alone was used as catalyst. After the reaction solution was concentrated, crystallization was carried out to obtain crystalline N-methylolacrylamide.

COMPARATIVE EXAMPLE 3

Reaction was carried out in the same manner as in Example 23 except that sodium hydroxide alone was used as catalyst. The reaction solution was cooled to crystallize crystalline N-methylolacrylamide.

COMPARATIVE EXAMPLES 4 AND 5

Reaction was carried out in the same manner as in Example 1 except that 0.8 g of triethylamine or 15 g of Amberlyst® A26, a strongly basic anion exchange resin, was used as catalyst.

The results in the above Examples and Comparative Examples will be shown in Table 1.

TABLE 1

| | Catalyst (mole %) | Acrylamide concentration (%) | Aqueous acrylamide solution (g) | Formaldehyde or paraformaldehyde (g) | Solvent | Reaction temperature (°C.) |
|---|---|---|---|---|---|---|
| Example 1 | Sodium hydroxide + sodium molybdate (0.02 + 0.04) | 81 | 74 | Paraformaldehyde 27.2 | Water | 50 |
| Example 2 | Sodium hydroxide + sodium tungstate (0.02 + 0.04) | 81 | 74 | Paraformaldehyde 27.2 | Water | 50 |
| Example | Potassium hydroxide + | 81 | 74 | Paraformal- | Water | 40 |

TABLE 1-continued

| | Catalyst | Reaction temperature | Reaction time | Formaldehyde | Solvent | Crystallization temperature |
|---|---|---|---|---|---|---|
| 3 | potassium molybdate (0.02 + 0.04) | | | dehyde 27.2 | | |
| Example 4 | Sodium hydroxide + sodium phosphotungstate (0.02 + 0.01) | 81 | 74 | Paraformaldehyde 26.7 | Water | 40 |
| Example 5 | Sodium silicate + sodium tungstate (0.01 + 0.06) | 81 | 74 | Paraformaldehyde 26.7 | Water | 40 |
| Example 6 | Sodium phosphate + sodium molybdate (0.02 + 0.07) | 81 | 74 | Paraformaldehyde 26.7 | Water | 50 |
| Example 7 | Sodium hydroxide + sodium molybdate (0.02 + 0.04) | 81 | 74 | 37% formalin 69.9 | Water | 60 |
| Example 8 | Sodium hydroxide + sodium molybdate + sodium tungstate (0.03 + 0.01 + 0.01) | 81 | 74 | Paraformaldehyde 27.2 | Water | 50 |
| Example 9 | Sodium hydroxide + sodium molybdate (0.03 + 0.06) | 81 | 74 | Paraformaldehyde 27.2 | Water/methanol (80/20) | 50 |
| Example 10 | Tetraethylammonium hydroxide (0.09) | 81 | 74 | Paraformaldehyde 27.2 | Water | 50 |
| Example 11 | Tetrabutylammonium hydroxide (0.04) | 81 | 74 | Paraformaldehyde 27.2 | Water | 40 |
| Example 12 | Trimethylbenzyl-ammonium hydroxide (0.04) | 81 | 74 | Paraformaldehyde 27.2 | Water | 60 |
| Example 13 | Trioctylmethyl-ammonium hydroxide (0.04) | 81 | 74 | 37% Formalin 69.9 | Water | 50 |
| Example 14 | Cetylpyridinium hydroxide (0.09) | 81 | 74 | Paraformaldehyde 26.7 | Water/methanol (80/20) | 50 |
| Example 15 | Sodium hydroxide + sodium molybdate (0.02 + 0.04) | 50 | 120 | Paraformaldehyde 27.2 | Water | 50 |
| Example 16 | Potassium hydroxide + potassium molybdate (0.02 + 0.04) | 30 | 200 | Paraformaldehyde 27.2 | Water | 40 |
| Example 17 | Sodium hydroxide + sodium tungstate (0.02 + 0.04) | 40 | 150 | Paraformaldehyde 27.2 | Water | 50 |
| Example 18 | Sodium hydroxide + sodium molybdate (0.02 + 0.04) | 50 | 120 | 37% Formalin 69.9 | Water | 60 |
| Example 19 | Sodium silicate + sodium tungstate (0.01 + 0.06) | 40 | 150 | Paraformaldehyde 26.7 | Water | 40 |
| Example 20 | Sodium hydroxide + sodium molybdate (0.02 + 0.07) | 50 | 120 | Paraformaldehyde 26.7 | Water | 50 |
| Example 21 | Sodium hydroxide + sodium phosphomolybdate (0.02 + 0.01) | 40 | 150 | Paraformaldehyde 26.7 | Water | 40 |
| Example 22 | Tetraethylammonium hydroxide (0.09) | 50 | 120 | Paraformaldehyde 27.2 | Water | 50 |
| Example 23 | Sodium hydroxide + sodium molybdate (0.02 + 0.04) | 81 | 74 | Paraformaldehyde 27.2 | Water | 50 |
| Comparative Example 1 | Sodium hydroxide (0.03) | 81 | 74 | Paraformaldehyde 27.2 | Water | 50 |
| Comparative Example 2 | Sodium hydroxide (0.03) | 50 | 120 | Paraformaldehyde 27.2 | Water | 50 |
| Comparative Example 3 | Sodium hydroxide (0.03) | 81 | 74 | Paraformaldehyde 27.2 | Water | 50 |
| Comparative Example 4 | Triethylamine (0.89) | 81 | 74 | Paraformaldehyde 27.2 | Water | 40 |
| Comparative Example 5 | Strongly basic anion exchange resin (7.10) | 81 | 74 | Paraformaldehyde 27.2 | Water | 40 |

| Reaction | pH of reaction | Reaction yield of N-methylolacrylamide | Reaction yield of by-products | Concentration of N-methylolacrylamide in | Crystallization tempera- | Yield of crystalline N-methylol- | Purity of crystalline N-methylol- |
|---|---|---|---|---|---|---|---|

TABLE 1-continued

|  | time (hr) | solution | in reaction solution (%) | in reaction solution (%) | concentrated solution (%) | ture (°C.) | acrylamide (g) | acrylamide (%) |
|---|---|---|---|---|---|---|---|---|
| Example 1 | 1.0 | 10.0 | 93.0 | 0.2 | — | — | — | — |
| Example 2 | 1.0 | 9.5 | 92.5 | 0.2 | — | — | — | — |
| Example 3 | 1.5 | 10.0 | 91.8 | 0.3 | — | — | — | — |
| Example 4 | 1.0 | 9.5 | 93.5 | 0.2 | — | — | — | — |
| Example 5 | 1.0 | 9.5 | 93.0 | 0.2 | — | — | — | — |
| Example 6 | 1.0 | 9.5 | 92.0 | 0.2 | — | — | — | — |
| Example 7 | 1.5 | 9.5 | 92.7 | 0.2 | — | — | — | — |
| Example 8 | 1.0 | 10.0 | 93.0 | 0.2 | — | — | — | — |
| Example 9 | 1.0 | 9.5 | 93.0 | 0.2 | — | — | — | — |
| Example 10 | 1.0 | 10.0 | 93.0 | 0.2 | — | — | — | — |
| Example 11 | 2.0 | 9.5 | 92.5 | 0.2 | — | — | — | — |
| Example 12 | 1.0 | 9.5 | 93.0 | 0.2 | — | — | — | — |
| Example 13 | 1.0 | 9.5 | 91.8 | 0.3 | — | — | — | — |
| Example 14 | 1.0 | 10.0 | 92.0 | 0.2 | — | — | — | — |
| Example 15 | 1.0 | 10.0 | 93.0 | 0.2 | 75 | 22 | 43.5 | 99.0 |
| Example 16 | 1.5 | 10.0 | 91.8 | 0.3 | 85 | 20 | 42.6 | 98.7 |
| Example 17 | 1.0 | 9.5 | 92.5 | 0.2 | 85 | 20 | 43.2 | 99.0 |
| Example 18 | 1.5 | 9.0 | 92.7 | 0.2 | 90 | 40 | 46.3 | 99.0 |
| Example 19 | 1.0 | 9.5 | 93.0 | 0.2 | 90 | 35 | 42.8 | 98.9 |
| Example 20 | 1.0 | 9.5 | 92.0 | 0.2 | 80 | 40 | 43.8 | 99.0 |
| Example 21 | 1.0 | 9.5 | 93.5 | 0.2 | 80 | 40 | 42.7 | 99.0 |
| Example 22 | 1.0 | 10.0 | 93.0 | 0.2 | 80 | 22 | 42.8 | 99.0 |
| Example 23 | 1.0 | 10.0 | 93.0 | 0.2 | — | 5 | 42.3 | 99.0 |
| Comparative Example 1 | 4.0 | 10.0 | 88.0 | 1.9 | — | — | — | — |
| Comparative Example 2 | 1.0 | 10.0 | 85.8 | 1.1 | 80 | 10 | 42.5 | 96.7 |
| Comparative Example 3 | 4.0 | 10.0 | 88.0 | 1.9 | — | 10 | 40.0 | 96.2 |
| Comparative Example 4 | 4.0 | 10.0 | 88.1 | 3.7 | — | — | — | — |
| Comparative Example 5 | 2.0 | 10.0 | 88.4 | 5.0 | — | — | — | — |

According to the method of the present invention, N-methylolacrylamide having few by-products is obtained in high yields. Also, high-purity crystalline N-methylolacrylamide is easily obtained using as direct material a 30 to 60% aqueous acrylamide solution which is easily available industrially. Further, the present invention has the following advantages:

(1) Purification is easy because of few by-products formed.

(2) Recycled use of the mother liquor after separation of crystalline N-methylolacrylamide is easy because of few by-products formed.

(3) Reaction time is shortened because of enhanced reaction rate.

(4) An aqueous acrylamide solution is used, so that there is no scattering of powder and handling is easy and safe.

(5) Crystals are obtained with a uniform and large particle size.

What is claimed is:

1. A method for producing N-methylolacrylamide which comprises reacting acrylamide with formaldehyde or paraformaldehyde in an aqueous solvent in the presence of (A) a basic compound and at least one member selected from the group consisting of a salt of Mo-containing acid and a salt of W-containing acid, or (B) a quaternary ammonium hydroxide compound.

2. A method according to claim 1, wherein the basic compound is one selected from the group consisting of hydroxides of alkali metals and alkaline earth metals, salts of alkali metals and alkaline earth metals, tertiary amines, metal alkoxides and basic anion exchange resins.

3. A method according to claim 1, wherein the salt of Mo-containing acid is one selected from the group consisting of alkali metal molybdates, alkali metal phosphomolybdates and alkali metal silicomolybdates.

4. A method according to claim 1, wherein the salt of W-containing acid is one selected from the group consisting of alkali metal tungstates, alkali metal phosphotungstates and alkali metal silicotungstates.

5. A method for producing N-methylolacrylamide which comprises reacting acrylamide in an aqueous acrylamide solution having a concentration of about 30 to about 60 wt. % with formaldehyde or paraformaldehyde in the presence of (A) a basic compound and at least one member selected from the group consisting of a salt of Mo-containing acid and a salt of W-containing acid, or (B) a quaternary ammonium hydroxide compound, concentrating the reaction solution under reduced pressure at a temperature of 80° C. or less and in a pH range of 6 to 8, cooling the concentrated solution and separating precipitated crystals.

6. A method according to claim 5, wherein the reaction solution is concentrated until the concentration of N-methylolacrylamide in it is in a range of 60 to 90 wt. %.

7. A method according to claim 5, wherein the basic compound is one selected from the group consisting of hydroxides of alkali metal and alkaline earth metals, salts of alkali metals and alkaline earth metals, teriary amines, metal alkoxides and basic anion exchange resins.

8. A method according to claim 5, wherein the salt of Mo-containing acid is one selected from the group consisting of alkali metal molybdates, alkali metal phosphomolybdates and alkali metal silicomolybdates.

9. A method according to claim 5, wherein the salt of W-containing acid is one selected from the group consisting of alkali metal tungstates, alkali metal phosphotungstates and alkali metal silicotungstates.

* * * * *